US005928925A

United States Patent [19]

Ito et al.

[11] Patent Number: 5,928,925
[45] Date of Patent: Jul. 27, 1999

[54] RICE ORNITHINE CARBAMYLTRANSFERASE GENE, AND A VECTOR CONTAINING SAID GENE AND A TRANSFORMANT

[75] Inventors: Yoshifumi Ito; Akihiro Hino; Hirohito Miura, all of Tsukuba, Japan

[73] Assignee: Director of National Food Research Institute, Ministry of Agriculture, Forestry and Fisheries, Tsukuba, Japan

[21] Appl. No.: 09/092,025

[22] Filed: Jun. 5, 1998

[30] Foreign Application Priority Data

Mar. 3, 1998 [JP] Japan .................................. 10-066070

[51] Int. Cl.$^6$ .............................. C12N 9/10; C12N 15/00; C12N 15/63; C12N 15/85

[52] U.S. Cl. ..................... 435/193; 435/69.1; 435/320.1; 435/325; 435/252.8

[58] Field of Search ................................ 435/193, 320.1, 435/69.1, 325, 252.8; 536/23.2

[56] References Cited

PUBLICATIONS

Williamson, C. et al., Genbank, Accession No. U13684, Aug. 1995.

*Primary Examiner*—Robert A. Wax
*Assistant Examiner*—Peter P. Tung
*Attorney, Agent, or Firm*—Oblon, Spivak, McClelland, Maier & Neustadt, P.C.

[57] ABSTRACT

An object of the present invention is to isolate complementary DNA coding for ornithine carbamyltransferase derived from a rice plant, necessary for development of a plant ornithine carbamyltransferase gene mutated to have phaseolotoxin resistance, and further to establish an expression system in microorganisms for simply evaluating the functions of the gene mutated to have resistance. This object is solved by a rice ornithine carbamyltransferase gene coding for a protein consisting of the amino acid sequence shown in SEQ ID NO:6 in the Sequence Listing, a plasmid vector containing the gene, and a transformant carrying the plasmid vector.

5 Claims, 1 Drawing Sheet

FIG.1

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 948 base pairs
      (B) TYPE: nucleic acid
      (C) STRANDEDNESS: single
      (D) TOPOLOGY: linear    (ii) MOLECULE TYPE: cDNA    (vi) ORIGINAL SOURCE:
      (A) ORGANISM: Rice (Oryza sative L.)
      (B) STRAIN: Nipponbare
      (C) INDIVIDUAL ISOLATE: Plasmid pOSOT9

(ix) FEATURE:
      (A) NAME/KEY: mat_peptide
      (B) LOCATION: 1..945
      (D) OTHER INFORMATION: /note= "METHOD OF DETERMINING
         FEATURE: E"

(ix) FEATURE:
      (A) NAME/KEY: CDS
      (B) LOCATION: 1..945

(xi) SEQUENCE DESCRIPTION: SEQ ID NO:1:

```
ATG TCG TCC TCT GCT GGT AAA GAT GCC AAA CAG ATT CCT AAG GAC TTT      48
Met Ser Ser Ser Ala Gly Lys Asp Ala Lys Gln Ile Pro Lys Asp Phe
 1               5                  10                  15

CTT CAT ATT GAT GAT TTC GAC AAG GAT ACA ATC ATG AAG ATC CTT AAT      96
Leu His Ile Asp Asp Phe Asp Lys Asp Thr Ile Met Lys Ile Leu Asn
                 20                  25                  30

CGG GCT ATT GAG GTC AAG GCA ATG ATA AAG TCA GGA GAC AGG AGC TTC     144
Arg Ala Ile Glu Val Lys Ala Met Ile Lys Ser Gly Asp Arg Ser Phe
             35                  40                  45

CAA CCT TTC AAA GGG AAA TCA ATG GCA ATG ATA TTT GCC AAG CCG TCA     192
Gln Pro Phe Lys Gly Lys Ser Met Ala Met Ile Phe Ala Lys Pro Ser
         50                  55                  60

ATG AGA ACC CGT GTT TCA TTT GAG ACA GGA TTC TTT TTG CTT GGT GGC     240
Met Arg Thr Arg Val Ser Phe Glu Thr Gly Phe Phe Leu Leu Gly Gly
 65                  70                  75                  80

CAT GCT ATC TAC CTG GGT CCT GAT GAT ATC CAG ATG GGC AAG CGT GAA     288
His Ala Ile Tyr Leu Gly Pro Asp Asp Ile Gln Met Gly Lys Arg Glu
                 85                  90                  95

GAG ACC GGT GAT GTT GCT CGT GTG CTT TCT GGA TAT AAT GAC ATC ATT     336
Glu Thr Gly Asp Val Ala Arg Val Leu Ser Gly Tyr Asn Asp Ile Ile
            100                 105                 110

ATG GCC AGG GTT TTT GCT CAC CAA GAC ATT TTG GAC TTG GCA AAG TAT     384
Met Ala Arg Val Phe Ala His Gln Asp Ile Leu Asp Leu Ala Lys Tyr
        115                 120                 125

GCA GCT GTA CCT GTC ATA AAT GGC CTT ACG GAC TAC AAC CAT CCA TGC     432
Ala Ala Val Pro Val Ile Asn Gly Leu Thr Asp Tyr Asn His Pro Cys
    130                 135                 140

CAG ATA ATG GCT GAT GCA CTT ACT ATG CTC GAA CAC ATT GGT CGT ATT     480
```

```
Gln Ile Met Ala Asp Ala Leu Thr Met Leu Glu His Ile Gly Arg Ile
145                 150                 155                 160

GAA AAC ACT AAG GTT GTC TAT GTT GGA GAC GGG AAC AAT ATT GTC CAC     528
Glu Asn Thr Lys Val Val Tyr Val Gly Asp Gly Asn Asn Ile Val His
                165                 170                 175

TCA TGG CTT CGA TTG GCT GCT TTA TTT CCT TTA CAT TTT GTA TGT GCC     576
Ser Trp Leu Arg Leu Ala Ala Leu Phe Pro Leu His Phe Val Cys Ala
            180                 185                 190

TGT CCT AAG GGC TTC GAG CCA GAT GCA AAG ACT GTG GAG ATA GCC AGG     624
Cys Pro Lys Gly Phe Glu Pro Asp Ala Lys Thr Val Glu Ile Ala Arg
        195                 200                 205

AGT GCT GGT AGT AAG ATT GAA ATA ACA GAT GAC CCT ATG GAA GCA GTT     672
Ser Ala Gly Ser Lys Ile Glu Ile Thr Asp Asp Pro Met Glu Ala Val
    210                 215                 220

AAG GGA GCA GAT GTT GTG TAT ACA GAT GTC TGG GCC AGC ATG GGC CAA     720
Lys Gly Ala Asp Val Val Tyr Thr Asp Val Trp Ala Ser Met Gly Gln
225                 230                 235                 240

AAG GAG GAA GCT GAA TAT AGA AAA AAA GTG TTC CAA GGA TTC ACG GTG     768
Lys Glu Glu Ala Glu Tyr Arg Lys Lys Val Phe Gln Gly Phe Thr Val
                245                 250                 255

GAT GAA GCT ATG ATG GAG ATG GCT GGG CCA AAT GCC TTC CTT ATG CAT     816
Asp Glu Ala Met Met Glu Met Ala Gly Pro Asn Ala Phe Leu Met His
            260                 265                 270

TGT TTG CCT GCA GAG AGA GGG ATA GAG GTA ACA GAC GGC GCC ATT GAA     864
Cys Leu Pro Ala Glu Arg Gly Ile Glu Val Thr Asp Gly Ala Ile Glu
        275                 280                 285

GCT CCC AAC TCA ATC GTA TTC CCC CAG GCT GAG AAC AGA ATG CAC GCC     912
Ala Pro Asn Ser Ile Val Phe Pro Gln Ala Glu Asn Arg Met His Ala
    290                 295                 300

CAG AAT GCT ATC ATG CTT CAC GTC CTT GGT GCT TAG                     948
Gln Asn Ala Ile Met Leu His Val Leu Gly Ala
305                 310                 315

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC OLIGONUCLEOTIDE"

(vi) ORIGINAL SOURCE:
        (A) ORGANISM: Rice (Oryza sative L.)
        (B) STRAIN: Nipponbare
        (C) INDIVIDUAL ISOLATE: Plasmid S4443

(ix) FEATURE:
        (A) NAME/KEY: misc_feature
        (B) LOCATION: 1..27
        (D) OTHER INFORMATION: /note= "SEQUENCE CHARACTER: mat
            peptide, METHOD OF DETERMINING THE CHARACTER: E"

(xi) SEQUENCE DESCRIPTION: SEQ ID NO:2:

CCGTCTCCAA CATAGACAAC CTTAGTG                                        27

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
```

(A) DESCRIPTION: /desc = "SYNTHETIC OLIGONUCLEOTIDE"

(vi) ORIGINAL SOURCE:
            (A) ORGANISM: Rice (Oryza sative L.)
            (B) STRAIN: Nipponbare
            (C) INDIVIDUAL ISOLATE: Plasmid S4443

(ix) FEATURE:
            (A) NAME/KEY: misc_feature
            (B) LOCATION: 1..27
            (D) OTHER INFORMATION: /note= "SEQUENCE CHARACTER: mat
                 peptide, METHOD OF DETERMINING THE CHARACTER: E"

(xi) SEQUENCE DESCRIPTION: SEQ ID NO:3:

TACATATGGT CGTCCTCTGC TGGTAAAG                                          28

(2) INFORMATION FOR SEQ ID NO:4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC OLIGONUCLEOTIDE"

(vi) ORIGINAL SOURCE:
            (A) ORGANISM: Rice (Oryza sative L.)
            (B) STRAIN: Nipponbare
            (C) INDIVIDUAL ISOLATE: Plasmid S4443

(ix) FEATURE:
            (A) NAME/KEY: misc_feature
            (B) LOCATION: 1..27
            (D) OTHER INFORMATION: /note= "SEQUENCE CHARACTER: mat
                 peptide, METHOD OF DETERMINING THE CHARACTER: E"

(xi) SEQUENCE DESCRIPTION: SEQ ID NO:4:

GTATGCAGCT GTACCTGTCA TAAATGG                                           27

(2) INFORMATION FOR SEQ ID NO:5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC OLIGONUCLEOTIDE"

(vi) ORIGINAL SOURCE:
            (A) ORGANISM: Rice (Oryza sative L.)
            (B) STRAIN: Nipponbare
            (C) INDIVIDUAL ISOLATE: Plasmid S4443

(ix) FEATURE:
            (A) NAME/KEY: misc_feature
            (B) LOCATION: 1..27
            (D) OTHER INFORMATION: /note= "SEQUENCE CHARACTER: mat
                 peptide, METHOD OF DETERMINING THE CHARACTER: E"

(xi) SEQUENCE DESCRIPTION: SEQ ID NO:5:

CTAAGCACCA AGGACGTGAA GCATG                                             25

(2) INFORMATION FOR SEQ ID NO:6:

(i) SEQUENCE CHARACTERISTICS:
            (A) LENGTH: 315 amino acids
            (B) TYPE: amino acid
            (D) TOPOLOGY: linear (ii) MOLECULE TYPE: protein (xi) SEQUENCE DESCRIPTION: SEQ ID NO:6:

```
Met Ser Ser Ser Ala Gly Lys Asp Ala Lys Gln Ile Pro Lys Asp Phe
 1               5                  10                  15

Leu His Ile Asp Asp Phe Asp Lys Thr Ile Met Lys Ile Leu Asn
                20                  25                  30

Arg Ala Ile Glu Val Lys Ala Met Ile Lys Ser Gly Asp Arg Ser Phe
                35                  40                  45

Gln Pro Phe Lys Gly Lys Ser Met Ala Met Ile Phe Ala Lys Pro Ser
            50                  55                  60

Met Arg Thr Arg Val Ser Phe Glu Thr Gly Phe Phe Leu Leu Gly Gly
 65                  70                  75                  80

His Ala Ile Tyr Leu Gly Pro Asp Asp Ile Gln Met Gly Lys Arg Glu
                85                  90                  95

Glu Thr Gly Asp Val Ala Arg Val Leu Ser Gly Tyr Asn Asp Ile Ile
                100                 105                 110

Met Ala Arg Val Phe Ala His Gln Asp Ile Leu Asp Leu Ala Lys Tyr
                115                 120                 125

Ala Ala Val Pro Val Ile Asn Gly Leu Thr Asp Tyr Asn His Pro Cys
            130                 135                 140

Gln Ile Met Ala Asp Ala Leu Thr Met Leu Glu His Ile Gly Arg Ile
145                 150                 155                 160

Glu Asn Thr Lys Val Val Tyr Val Gly Asp Gly Asn Asn Ile Val His
                165                 170                 175

Ser Trp Leu Arg Leu Ala Ala Leu Phe Pro Leu His Phe Val Cys Ala
                180                 185                 190

Cys Pro Lys Gly Phe Glu Pro Asp Ala Lys Thr Val Glu Ile Ala Arg
                195                 200                 205

Ser Ala Gly Ser Lys Ile Glu Ile Thr Asp Asp Pro Met Glu Ala Val
            210                 215                 220

Lys Gly Ala Asp Val Val Tyr Thr Asp Val Trp Ala Ser Met Gly Gln
225                 230                 235                 240

Lys Glu Glu Ala Glu Tyr Arg Lys Lys Val Phe Gln Gly Phe Thr Val
                245                 250                 255

Asp Glu Ala Met Met Glu Met Ala Gly Pro Asn Ala Phe Leu Met His
                260                 265                 270

Cys Leu Pro Ala Glu Arg Gly Ile Glu Val Thr Asp Gly Ala Ile Glu
            275                 280                 285

Ala Pro Asn Ser Ile Val Phe Pro Gln Ala Glu Asn Arg Met His Ala
            290                 295                 300

Gln Asn Ala Ile Met Leu His Val Leu Gly Ala
305                 310                 315
```

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:7:

```
Ser Ser Ser Ala Gly Lys Asp Ala Lys Gln
 1               5                  10
```

RICE ORNITHINE CARBAMYLTRANSFERASE GENE, AND A VECTOR CONTAINING SAID GENE AND A TRANSFORMANT

FIELD OF THE INVENTION

The present invention relates to an ornithine carbamyltransferase gene derived from a rice plant, as well as a plasmid vector containing said gene and a transformant.

BACKGROUND OF THE INVENTION

Ornithine carbamyltransferase is an enzyme in a pathway for biosynthesizing arginine, which catalyzes the reaction of forming citrulline by transferring a carbamyl group from carbamylphosphate to ornithine.

Phaseolotoxin produced by a plant-pathogenic microorganism *Pseudomonas syringae* pv. *phaseolicola* inhibits ornithine carbamyltransferase activity. Hence, plants infected with this microorganism or plants sprayed with phaseolotoxin are prevented from being supplied with arginine necessary for protein synthesis, and cell growth is terminated and the plant will be withered at last.

The present invention relates to a rice-derived ornithine carbamyltransferase gene which can be utilized in creating a gene coding for plant ornithine carbamyltransferase having resistance to an inhibitory compound such as phaseolotoxin targeting ornithine carbamyltransferase, as well as in efficient production of an enzyme used in screening an inhibitory compound targeting plant ornithine carbamyltransferase.

*Pseudomonas syringae* pv. *phaseolicola* is a plant-pathogenic microorganism carrying a gene for ornithine carbamyltransferase having resistance to self-produced phaseolotoxin.

A recombinant plant having this phaseolotoxin-resistant ornithine carbamyltransferase gene introduced thereinto is reported to exhibit resistance to pathogenic *Pseudomonas syringae* (Hatziloukas, E. and Panopoulos, N. J., J. Bacteriol., 172: 5895–5909, 1992). However, said gene is derived from the plant-pathogenic microorganism and has, therefor, a potential safety problem in practical use. Accordingly, said gene is not applied to edible crops.

On the other hand, an ornithine carbamyltransferase gene derived from plants, particularly from edible crops, is superior in safety as a practical gene to be introduced. If a mutation can be introduced in this ornithine carbamyltransferase gene from edible crops to create phaseolotoxin resistant ornithine carbamyltransferase, it would be possible to develop a practical ornithine carbamyltransferase gene for producing plants resistant to the toxin.

For development of the plant ornithine carbamyltransferase gene mutated so as to have phaseolotoxin resistance, it is necessary to obtain complementary DNA coding for said enzyme from edible crops. Further, it is necessary to establish an expression system, e.g. in microorganisms, for easily evaluating the functions of said resistant gene.

However, plant complementary DNA proven to code for said enzyme, or an expression system for verifying it, still remains unsolved.

The object of the present invention is to isolate complementary DNA coding for ornithine carbamyltransferase derived from a rice plant, necessary for development of a plant ornithine carbamyltransferase gene mutated to have phaseolotoxin resistance and further to establish an expression system in microorganisms for simply evaluating the functions of said gene mutated to have said resistance.

Incidentally, the use of phaseolotoxin as a herbicidal component in utilizing its inhibitory activity on ornithine carbamyltransferase is examined.

Conventionally, evaluation of the herbicidal activity of such compounds has been carried out by observing physiological alternations as a symptom appearing on a plant sprayed with test compounds. Accordingly, the evaluation process of herbicidal acitivity costs a great deal of time and labor including cultivation of test plants.

In order to develop rapid and easy in vitro evaluation system for potential herbicidal compounds, a means of producing a large amount of rice ornithine carbamyltransferase is necessary, for which it is also necessary to obtain complementary DNA coding for said enzyme.

SUMMARY OF THE INVENTION

As a result of their eager study to achieve the above object, the present inventors succeeded in obtaining the complementary DNA coding for a mature part of ornithine carbamyltransferase by joining a newly obtained complementary DNA clone coding for a N-terminal region of ornithine carbamyltransferase to a complementary DNA clone coding for a C-terminal region of ornithine carbamyltransferase isolated from a rice complementary DNA library constructed by a rice genome project in the Ministry of Agriculture, Forestry and Fisheries, Japan.

That is, the present inventors determined the whole nucleotide sequence of S4443 clone isolated by the rice genome project, and they revealed that said clone codes for the C-terminal region (206-amino-acid residue) of rice ornithine carbamyltransferase. Further, the N-terminal region (340 bp) was cloned by the 5' Race method using complementary DNA, as a template, synthesized from messenger RNA prepared from rice callus.

These sequences were ligated to give complementary DNA for a catalytic region of said enzyme.

The complementary DNA thus obtained was re-cloned in *E. coli* plasmid pUC118 and transformed into *E. coli* deficient in an ornithine carbamyltransferase gene. As a result, the present inventors demonstrated that rice ornithine carbamyltransferase is expressed in *E. coli*, functions as an arginine biosynthetic enzyme in *E. coli* cells, and has ornithine carbamyltransferase activity, thereby arriving at the completion of the present invention.

The invention described in claim 1 is an isolated rice ornithine carbamyltransferase gene coding for a protein consisting of the amino acid sequence shown in SEQ ID NO:1 in the Sequence Listing.

The invention described in claim 2 is a plasmid vector comprising the rice ornithine carbamyltransferase gene of claim 1.

The invention described in claim 3 is a transformant carrying the plasmid vector of claim 2.

BRIEF DESCRIPTION OF THE DRAWING

FIG. 1 is a photograph showing a profile in electrophoresis of purified rice ornithine carbamyltransferase expressed in *E. coli.*

In FIG. 1, the numerical values in the left are their corresponding molecular weights (unit: kDa); M at the left lane is a molecular marker; 1 is the enzyme after purification on a Bio-Scale DEAE column; and 2, after purification on a gel filtration column.

DETAILED DESCRIPTION OF THE INVENTION

Hereinafter, the present invention is described in detail.

The ornithine carbamyltransferase complementary DNA according to the present invention is a part of a DNA sequence derived from a rice plant.

The present inventors searched a complementary DNA sequence in a DNA data base which has homology to complementary DNA sequence estimated to encode pea-derived ornithine carbamyltransferase.

As a result, it was found that a partial sequence (340 bp) of S4443 clone has 80% homology to the complementary DNA estimated to code for ornithine carbamyltransferase derived from peas.

Then, the whole nucleotide sequence of this complementary DNA from the S4443 clone was determined.

Nucleotide sequencing can be achieved by conventional means. For example, sequencing reaction is carried out using a dye primer cycle sequencing kit (Parkin Elmer) with S4443 clone DNA as a template prepared using a Flex-prep plasmid forming kit (Pharmacia). Then, an ABI377 DNA sequencer (Parkin Elmer) can be used to determine the nucleotide sequence.

Preparation of the plasmid DNA used as said template can also be done by the alkali-SDS method (Sambrook, J., Fritsch, E. F. and Maniatis, T., Molecular Cloning, A Laboratory Manual, Cold Spring Harbor Laboratory Press, New York, 1989).

Alternatively, nucleotide sequencing can also be conducted by methods such as the Sanger method (Sanger, F., Nicklen, S. and Coulson, A. R., Proc. Natl. Acad. Sci. USA, 74: 5463–5467, 1977) and the Maxam-Gilbert method (Maxam, A. M. and Gilbert, W., Methods Enzymol., 65: 499–560, 1980).

As a result, it was revealed that it is highly possible that the S4443 clone codes for the C-terminal region (206-amino-acid residue) of rice ornithine carbamyltransferase.

Then, complementary DNA coding for the N-terminal region was obtained and analyzed.

Rice RNA was first prepared, and messenger RNA was then purified therefrom.

Rice RNA can be obtained from rice callus cultured in various media such as MS medium (Plant Biotechnology (1986) edited by Yamada, Y. and Okada, Y. and published by Tokyo Kagaku Dojin).

As the means of preparing RNA, it is possible to employ the SDS-phenol method (Takaiwa, F., Kikuchi, S. and Ohno, K., Mol. Gene. Genet., 208: 15–22, 1987), the guanidine thiocyanate method (Puissant, C. and Houdelbine, L. M., Biotechniques, 8: 148–149, 1990), the cesium chloride density gradient centrifugation (Groppe, J. C. and Morse, D. E., Anal. Biochem., 210: 337–343, 1993) and the like.

From the resulting RNA, messenger RNA was prepared by means of Oligotex-dT30 (super) (Takara Co., Ltd.) or the like.

A first strand was synthesized with the messenger RNA as a template by use of a Marathon cDNA Amplification kit (Clonetech) and subsequently a second strand was synthesized.

The first strand could be obtained by reaction of moloney murine leukemia virus (MMLV) reverse transcriptase in a reaction solution containing the messenger RNA, dNTP and a Marathon cDNA primer.

Then, the second strand could be obtained by allowing RNase H and Klenow enzyme to act on the first strand in the presence of dNTP.

The resulting double-stranded DNA strands were ligated with Marathon cDNA adaptors.

Polymerase chain reaction (PCR) was conducted using this complementary DNA as a template. Oligonucleotide OSOT-C (see SEQ ID NO: 2 in the Sequence Listing, manufactured by Hokkaido System Service K.K.) consisting of a complementary sequence of the 159- to 165-positions in the S4443 clone and an AP1 primer (Clonetech) were used as the primers for this PCR.

The DNA fragment thus amplified was cleaved with a restriction enzyme (NotI) and cloned into vector plasmid pBluescript SK(+) stratagene previously cleaved with NotI and PvuII whereby recombinant plasmid POSOT4 was obtained.

As a result of sequencing of the DNA fragment cloned in POSOT4, the fragment was revealed to contain a sequence of from the 1- to 185-positions and a 340-bp 5'-upstream region from the S4443 clone.

Subsequently, said two complementary DNAs coding for the N- or C-terminal regions of rice ornithine carbamyltransferase were ligated in the following manner to prepare one continuous complementary DNA.

First, 15 cycles of PCR for amplification was carried out using plasmid pOSOT4 containing the complementary DNA coding for the N-terminal region as a template and oligonucleotides OSOT-D (see SEQ ID NO:3 in the Sequence Listing, manufactured by Hokkaido System Service K.K.) and OSOT-C (see SEQ ID NO:2 in the Sequence Listing, manufactured by Hokkaido System Service K.K.) as primers.

Here, OSOT-D is an oligonucleotide synthesized such that GTG codon for amino acid residue Val at the 5-position in the protein encoded by the complementary DNA coding for the N-terminal region is replaced by the translation initiation codon ATG and that the ATG sequence serves as a sequence to be cleaved with restriction enzyme NdeI.

Similarly, 15 cycles of PCR were carried out using the S4443 clone as a template and OSOT-A (see SEQ ID NO:4 in the Sequence Listing) and OSOT-B (see SEQ ID NO:5 in the Sequence Listing) as primers to amplify a sequence of from the 381- to 948-positions in SEQ ID NO:5.

Two DNA fragments obtained as amplification products in the twice-conducted PCR amplification were mixed, and OSOT-D and OSOT-B were added as primers thereto, and 25 cycles of PCR were further carried out.

In the above thrice-conducted PCR, KOD polymerase (Toyobo) was used as DNA polymerase under the conditions recommended by Toyobo.

The resulting 948-bp DNA fragment having the sequence shown in SEQ ID NO:1 in the Sequence Listing is a complementary DNA constituting the rice ornithine carbamyltransferase gene of the present invention.

The above method is just one example, and the complementary DNA having the same sequence as in the present invention can also be obtained from the rice complementary library by other methods such as colony or plaque hybridization method where a DNA complementary to S4445 is used as a probe (Sambrook, J., Fritsch, E. F. and Maniatis, T., Molecular Cloning, A Laboratory Manual, Cold Spring Harbor Laboratory Press, New York, 1989) etc.

The complementary DNA contained in the gene of the present invention was used in the following operation to produce a plasmid vector and transformant.

First, the complementary DNA was cloned in the HincII site of plasmid pUC118. to produce pOSOT9.

From pOSOT9, ornithine carbamyltransferase complementary DNA was isolated as an NdeI-HindIII fragment and cloned in the NdeI-HindIII site of *E. coli* expression vector PET-22b (+) (Novagen).

The resulting plasmid POSOT10 was transformed into *E. coli* BL21 (DE3) (Studier, F. W. and Moffatt, B. A., J. Mol. Biol., 189: 113–130 (1986)).

Transformation can be performed in a usual manner e.g. the calcium chloride method (Cohen, S. N. Chang, A. C. Y. and Hsu, L., Proc. Natl. Acad. Sci. USA, 69: 2110–2114, 1972), the electroporation method ("Shin Kiso Seikagaku Jikkenho" (New Experimental Methods in Biochemistry), Genetic Engineering (1988) edited by S., Miura et al. and published by Maruzen K. K.) etc.

The transformed *E. coli* was deposited under the terms of the Budapest Treaty on Feb. 18, 1998 as FERM BP-6260 with the National Institute of Bioscience and Human-Technology, Agency of Industrial Science and Technology, Japan.

Expression of the rice ornithine carbamyltransferase gene of the present invention can be confirmed by determining the amino acid sequence of the enzyme produced by this transformed *E. coli* or by measuring ornithine carbamyltransferase activity in said *E. coli*.

It was thus demonstrated that the rice ornithine carbamyltransferase gene of the present invention codes for ornithine carbamyltransferase. Up to now, there has been no example revealing that plant ornithine carbamyltransferase is expressed in *E. coli* and demonstrates its functions. Further, it was revealed for the first time by the present invention that a large amount of plant ornithine carbamyltransferase can be expressed in *E. coli* and purified from it.

According to the present invention, there is provided a complementary DNA coding for ornithine carbamyltransferase derived from a rice plant. By use of this complementary DNA, a highly safe ornithine carbamyltransferase gene mutated to have phaseolotoxin resistance can be developed and expected for its application to edible plants.

According to the present invention, there is further provided a transformant carrying the complementary DNA coding for rice ornithine carbamyltransferase. This transformant can be utilized effectively as an expression system in microorganisms for simply and easily evaluating the functions of the ornithine carbamyltransferase gene mutated to have phaseolotoxin resistance.

Furthermore, ornithine carbamyltransferase can be produced in a large amount on the basis of the complementary DNA of the present invention. By use of a large amount of the enzyme thus produced, evaluation of the herbicidal activity of compounds having inhibitory activity on ornithine carbamyltransferase, such as phaseolotoxin etc as active ingredients in herbicides can be effected readily in a rapid in vitro assay without using any plant for evaluation.

EXAMPLES

Hereinafter, the present invention is described in more detail by reference to the Examples.

Example 1

A complementary DNA sequence estimated to code for ornithine carbamyltransferase derived from peas was used to examine for its homology to DNA sequences registered in a DNA data base.

As a result, it was found that a partial sequence (340 bp) of S4443 clone isolated by the above-mentioned rice genome project has 80% homology to the complementary DNA estimated to code for ornithine carbamyltransferase derived from peas.

Then, the whole nucleotide sequence of the complementary DNA of the S4443 clone was determined. That is, sequencing reaction was carried out using a dye primer cycle sequencing kit (Parkin Elmer) with S4443 clone DNA as a template prepared using a Flex-prep plasmid forming kit (Pharmacia), and the whole nucleotide sequence of the complementary DNA of the S4443 clone was determined in an AB1377 DNA sequencer (Parkin Elmer).

The result indicated that it is highly possible that the S4443 clone codes for the C-terminal region (206-amino-acid residue) of rice ornithine carbamyltransferase.

Then, complementary DNA coding for a N-terminal region of rice ornithine carbamyltransferase was obtained in the following manner.

Callus of a rice plant (variety: Nipponbare) at the growth phase, cultured in MS medium (Plant Biotechnology (1986) edited by Yamada, Y. and Okada, Y. and published by Tokyo Kagaku Dojin), were used to prepare total RNA by the SDS-phenol method (Takaiwa, F., Kikuchi, S. and Ohno, K., Mol. Gene, Genet., 208: 15–22, 1987), and messenger RNA was further prepared therefrom using Oligotex-dT30 (super) (Takara Co., Ltd.).

A first strand of the complementary DNA was synthesized with the messenger RNA as a template by use of a Marathon cDNA Amplification kit (Clonetech) and subsequently a second strand was synthesized. That is, the first strand was synthesized by allowing moloney murine leukemia virus (MMLV) reverse transcriptase to react at 42° C. for 1 minute in a 10 $\mu$L reaction solution containing 1 $\mu$g of the messenger RNA, 10 mM dNTP and 1 $\mu$M Marathon cDNA primer (Clonetech).

Then, the second strand was synthesized by allowing RNase H and Klenow enzyme to act on the first strand in the presence of dNTP.

A Marathon cDNA adapter was linked by T4 DNA ligase to both ends of the synthesized double-stranded DNA.

Oligonucleotide OSOT-C (see SEQ ID NO:2 in the Sequence Listing) consisting of a complementary sequence of from the 159- to 165-positions from the S4443 clone was synthesized using a phosphoamidide reagent (Parkin Elmer) (this synthesis was entrusted to Hokkaido System Service K.K.). Polymerase chain reaction was conducted using this OSOT-C and an AP1 primer (Clonetech) with the previously synthesized double-stranded complementary DNA as a template.

The DNA fragment thus amplified was cleaved with restriction enzyme NotI and cloned in vector plasmid pBluescript SK(+) stratagene previously cleaved with restriction enzymes NotI and PvuII.

As a result of sequencing the DNA fragment cloned in the recombinant plasmid pOSOT4 obtained in the above-described method, the fragment was revealed to contain a sequence of from the 1- to 185-positions and a 340-bp 5'-upstream region derived from the S4443 clone.

Then, the two complementary DNAs coding for the N- or C-terminal regions of rice ornithine carbamyltransferase were ligated in the following manner to prepare one continuous complementary DNA.

First, 15 cycles of PCR for amplification was carried out using plasmid pOSOT4 containing the complementary DNA coding for the N-terminal region as a template and oligonucleotides OSOT-D (see SEQ ID NO:3 in the Sequence Listing, manufactured by Hokkaido System Service K.K.) and OSOT-C (see SEQ ID NO:2 in the Sequence Listing, manufactured by Hokkaido System Service K.K.) as primers. Here, OSOT-D is an oligonucleotide synthesized such that GTG codon for amino acid residue Val at the 5-position in the protein encoded by the complementary DNA coding for the N-terminal region is replaced by the translation initiation codon ATG and that the ATG sequence serves as a sequence to be cleaved with restriction enzyme NdeI.

Similarly, 15 cycles of PCR were carried out using the S4443 clone as a template and OSOT-A (see SEQ ID NO:4 in the Sequence Listing) and OSOT-B (see SEQ ID NO:5 in the Sequence Listing) as primers.

The resulting two DNA fragments were mixed, and OSOT-D and OSOT-B were added as primers thereto, and 25 cycles of PCR were further carried out.

In said thrice-conducted PCR, KOD polymerase (Toyobo) was used as DNA polymerase under the conditions recommended by Toyobo.

As a result, the 948-bp DNA fragment (see SEQ ID NO:1 in the Sequence Listing) was obtained. In this fragment, a sequence of from the 1- to 512-positions in SEQ ID NO:1 in the Sequence Listing is derived from the product in PCR with pOSOT4 as a template and a sequence of from the 381- to 948-positions is derived from the product in PCR with the S4443 clone as a template.

The DNA fragment having the sequence of SEQ ID NO:1 was cloned in the HincII site of plasmid pUC118, to produce pOSOT9. It was confirmed by DNA sequencing that the amplified sequence is the same as the sequence described in SEQ ID NO:5 in the Sequence Listing.

E. coli CM236 strain was transduced with pOSOT9 by the calcium chloride method (Cohen, S. N., Chang, A. C. Y. and Hsu, L., Proc. Natl. Acad. Sci. USA, 69: 2110–2114, 1972).

Because E. coli CM236 strain is deficient in two genes i.e. argF and ArgI coding for ornithine carbamyltransferase, this microorganism cannot produce said enzyme (Jeenes, D. J., Soldati, L., Baur, H., Mercenier, A., Reimmann, C., Leisinger, T. and Haas, D., Mol. Gen. Genet., 203: 421–429 (1986)).

Ornithine carbamyltransferase is an enzyme catalyzing the synthesis of citrulline as an intermediate for biosynthesis of arginine, so CM236 strain, which is free of this enzyme, cannot synthesize citrulline as a biosynthetic intermediate of arginine and thus shows an arginine-requiring phenotype.

CM236 strain, CM236 strain carrying vector plasmid pUC118, and CM236 strain carrying plasmid pOSOT9 containing the rice ornithine carbamyltransferase complementary DNA were examined for their growth in the absence and presence of arginine.

The medium used was M9 minimum medium containing glucose as a carbon source and ammonia chloride as a nitrogen source (Sambrook, J., Fritsch, E. F. and Maniatis, T., Molecular Cloning: A Laboratory Manual, 2nd ed. Cold Spring Harbor Laboratory, New York, 1989).

As a result, all the strains grew in the M9 medium in the presence of 1 mM arginine, while only the CM236 strain carrying pOSOT9 grew in the arginine-free M9 medium.

From this result, it was concluded that the rice complementary DNA cloned in pOSOT9 encodes ornithine carbamyltransferase functioning in cells.

Further, the ornithine carbamyltransferase complementary DNA was isolated as an NdeI-HindIII fragment from pOSOT9 and cloned in the NdeI-HindIII site of E. coli expression vector pET-22b (+) (Novagen).

Plasmid pOSOT10 thus obtained was transformed into E. coli BL21 (DE3) (Studier, F. W. and Moffatt, B. A., J. Mol. Biol., 189: 113–130 (1986)). BL21 (DE3) carrying pOSOT10 was cultured in LB medium (Sambrook, J., Fritsch, E. F. and Maniatis, T., Molecular Cloning: A Laboratory Manual, 2nd ed. Cold Spring Harbor Laboratory Press, New York, 1989), and expression of the enzyme in the cells was induced by adding isopropyl-$\beta$-thiogalactopyranoside (IPTG) to the cultures at an initial logarithmic growth phase and then incubating the cultures for 3 hours. The cells were collected by centrifugation and disrupted with a French press (Amicon) to prepare an enzyme solution. The enzyme solution was purified through a Bio-Scale DEAE column (Bio-Rad) and then through a gel filtration column (Superrose 12HR, available from Pharmacia).

Figure 1:
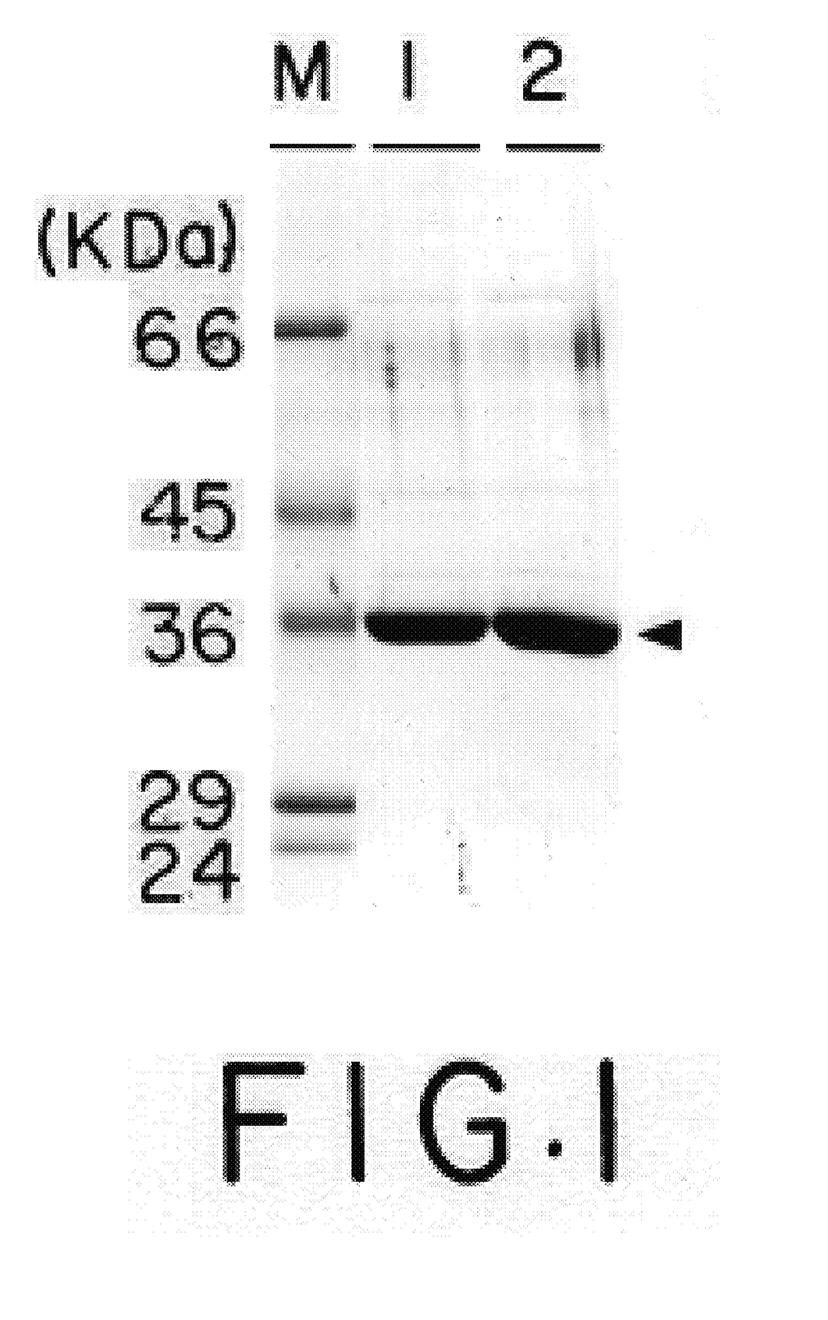

The result of SDS polyacrylamide gel electrophoresis of the enzyme after each purification step is shown in FIG. 1. In the profile in FIG. 1, the left lane (M) is a molecular-weight marker; lane 1, the enzyme after purification on the Bio-Scale DEAE column; and lane 2, the enzyme after purification on the gel filtration column (Superrose 12HR, Pharmacia).

The properties of the rice ornithine carbamyltransferase thus obtained are as follows:

Molecular weight:
    Monomer: 35,000 dalton
    Active form: 240,000 dalton (hexamer)
N-terminal amino acid sequence: Ser-Ser-Ser-Ala-Gly-Lys-Asp-Ala-Lys-Gln (SEQ ID NO:7)
Optimum pH: 7.5
Km for ornithine: 3.0 mM
Specific activity: 13 $\mu$mole citrulline/min./mg protein.

As described above, the N-terminal amino acid sequence of the purified enzyme was in complete agreement with the sequence (amino acid sequence corresponding to the nucleotide sequence between the 4 and 33 positions in SEQ ID NO:1 in the Sequence Listing) predicted from the nucleotide sequence of the enzyme. Further, it was found that this enzyme has high enzyme activity, and has the ability to catalyze the reaction of forming citrulline by transferring a carbamyl group from carbamylphosphate to ornithine.

The above results demonstrated that the complementary DNA of the present invention codes for ornithine carbamyltransferase. Up to now, there is no example showing that plant ornithine carbamyltransferase is expressed in E. coli and demonstrates its functions. Further, it was revealed for the first time by the present invention that a large amount of plant ornithine carbamyltransferase can be expressed in *E. coli* and purified from it.

The transformed *E. coli* has been deposited as FERM BP-6260 with the National Institute of Bioscience and Human-Technology, Agency of Industrial Science and Technology.

The entire disclosure of Japanese Patent Application No. 10-66070 filed on Mar. 3, 1998 including specification, claims and summary are incorporated herein by reference in its entirety.

What is claimed is:

1. An isolated DNA encoding rice ornithine carbamyltransferase having the amino acid sequence of SEQ ID NO: 6.

2. A vector comprising the DNA of claim 1.

3. A transformant containing the vector of claim 2.

4. The transformant according to claim 3 which is FERM BP-6260.

5. A method of producing rice ornithine carbamyltransferase comprising culturing the transformant of claim 3 in a culture medium and isolating the rice ornithine carbamyltransferase.

* * * * *